(12) United States Patent
Haider

(10) Patent No.: US 8,145,664 B2
(45) Date of Patent: Mar. 27, 2012

(54) DISEASE ORIENTED USER INTERFACES

(75) Inventor: Sultan Haider, Erlangen (DE)

(73) Assignee: Siemens Aktiengesellschaft, Munich (DE)

(*) Notice: Subject to any disclaimer, the term of this patent is extended or adjusted under 35 U.S.C. 154(b) by 849 days.

(21) Appl. No.: 12/192,219

(22) Filed: Aug. 15, 2008

(65) Prior Publication Data

US 2010/0042436 A1 Feb. 18, 2010

(51) Int. Cl.
G06F 17/30 (2006.01)
(52) U.S. Cl. .......................... 707/769; 707/770
(58) Field of Classification Search .................. 707/610, 707/690, 705, 769, 770
See application file for complete search history.

(56) References Cited

U.S. PATENT DOCUMENTS

| 2005/0075904 A1* | 4/2005 | Wager et al. ...................... 705/2 |
| 2005/0275871 A1* | 12/2005 | Baird et al. .................. 358/1.15 |
| 2007/0116036 A1* | 5/2007 | Moore .......................... 370/462 |
| 2009/0217340 A1* | 8/2009 | Sitomer et al. .................... 726/1 |

* cited by examiner

*Primary Examiner* — Charles Rones
*Assistant Examiner* — Fariborz Khoshnoodi

(57) ABSTRACT

There is provided a method and system for case-specific information retrieval from a medical database system. The information to be retrieved comprises at least two categories, clinical guidelines related information and patient related information. The method comprises the steps of accessing a database for retrieval of the clinical guidelines related information and accessing a database for retrieval of the patient related data; matching the accesses; displaying the retrieved clinical guidelines related information and the patient related information and the matched pairs of accesses.

13 Claims, 3 Drawing Sheets

DISEASE ORIENTED USER INTERFACES

TECHNICAL FIELD

The present invention relates generally to medical information retrieval and more particularly to user interfaces for displaying the retrieved medical information.

BACKGROUND OF THE INVENTION

In modern medical facilities patient related data are almost exclusively recorded and stored as electronic data files. The electronic health record (EHR) is one example.

The EHR includes images, lab reports, etc. and is kept in storage facilities that are interconnected in a network with a number of workstations.

Medical practitioners use the workstations to access and to retrieve patient related data for research or for the purposes of diagnosis.

Advances in the medical field led to the development of dedicated medical imaging equipment also known as modalities. Examples are computer tomographs (CT) and magnetic resonance imaging (MRI) modalities. The modalities allow the acquisition of highly specific images for the purposes of diagnoses of specific diseases.

The modalities allow the medical practitioner acquiring images tailored for the purposes of diagnosing a specific disease.

In order to diagnose another disease further images with possible different parameter settings on the same modality must be taken or one resorts to another modality altogether.

Thanks to modern medical research it is possible for people nowadays to live much longer than they did in the past. However, this comes at the expense that people contract a number of different diseases during their long lives.

Most of the diseases afflicting the elderly are chronic is diseases.

The combined effect of the large number of different diseases per person and the large number of different images acquired for diagnosing each of the different disease results in an exponential growth of medical image data in the storage facilities. Disease-targeted retrieval and interpretation thereof becomes a daunting task.

Moreover, advances in medical research also generate an ever growing stream of new medical knowledge disseminated for example through medical journals. This knowledge leads to equally constant up- or outdating of medical guidelines.

Therefore it becomes more and more difficult for the medical practitioner to interpret and to evaluate the vast number of available patient related information against the constantly updated medical knowledge in the guidelines. This difficulty undermines the efficiency of the diagnostic work.

Accordingly there is a need for an improved and time-efficient method for making available patient related medical information and taking at the same time into account the constantly updated stream medical knowledge in the medical guidelines.

SUMMARY OF THE INVENTION

The above identified need is addressed by the present invention in providing a method for case specific information retrieval from a medical database system. The information to be retrieved comprises at least two categories, including guidelines related information and patient related information. The inventive method comprises:

Accessing a database for retrieval of the clinical guidelines related information;

Accessing a database for retrieval of patient related information;

Matching the accesses, that is, matching the accesses to clinical guidelines related information and patient related information;

Displaying the retrieved clinical guidelines related information and the patient related information and the matched pairs of accesses.

"Case specific information" will be construed as relating to information specific to the medical history of a specific patient having regard to medical knowledge.

Under the term "clinical guidelines related information" is meant clinical knowledge structured into rules or tables as frequently employed in case-based reasoning systems.

The rules are essentially expressed as pairs of an antecedent and a corresponding consequent.

The antecedent specifies patient related and medical characteristics such as age, sex, and previous conditions etc.

The consequent specifies related medical actions to be taken. The actions may comprise administration of certain medication or other curative actions.

The consequent may also prohibit certain medication to be administrated or certain curative actions to be taken given for example a certain age.

The term "patient related information" should be taken to a comprise information from a specific patient's health record. The patient related information is of the type of information to be found in the above mentioned antecedents in the clinical guidelines related information.

The terms "access" or "accessing" are to be construed to comprise actions related to locating information for example providing information in databases and making that information available for comparative data operations such as matching etc. The term "accessing" is further to include "retrieving operations". By retrieving operations are operations of actually transferring the accessed information from a source such as a database to a target in the network from which the access has been requested, such as a workstation.

The term "displaying" comprises routines for arranging the retrieved information on a computer screen or on other suitable output devices, like portable PDAs etc.

The method according to the present invention allows displaying the patient related information along with the dynamically updated clinical guidelines related information as applicable to the patient related information.

According to one aspect of the present invention the clinical guidelines related information and the patient related information is stored in different segments of the same or in different databases.

This allows applying the method according to the invention to different infrastructural information technology requirements.

According to a further aspect of the present invention the clinical guidelines related information comprises additional information in particular metadata related to patients. The metadata comprises information related to a geographical area in which the patient resides or is a national of.

According to one aspect of the present invention this metadata can be used to adapt the inventive method of displaying case specific information specific to the geographical area. This allows qualifying certain curative actions implied by the clinical guidelines with respect to geo-specific physiological characteristics of patients from that geographical area.

According to another aspect of the present invention the inventive step further comprises:

Monitoring the clinical guidelines related information for updates, the monitoring being triggered by time or by other configurable events.

Monitoring for updates allows keeping pace with advances in the medical field and to make sure that only the most recent guideline related information is displayed and applied to the patient related information.

According to a further aspect of the invention the displaying further comprises in case of a match displaying the match in a highlighted manner. Matching and highlighting are one way of applying the guideline related information to the patient related information as envisaged by the present invention.

According to yet another aspect of the present invention the accesses to the databases is matched along with the accessed guideline related and patent related information.

According to another aspect of the present invention the matches a qualified with respect to configurable weight factors. This allows the user to assign certain weight factors to certain ones of the antecedences he or she considers most important when matching against the patient related information.

According to yet another aspect of the present invention the step of displaying further comprises:

Comparing the retrieved clinical guidelines related information and the patient related information with reference values.

In case the retrieved clinical guidelines related information and the patient related information do not comply with their respective reference values the corresponding non compliant guidelines related information or the patient related information are flagged.

This allows drawing the medical practitioner's attention in an efficient manner to possibly life threatening deviations of the patient related information from the normal.

The present invention furthermore addresses the above mentioned needs in providing a computer readable medium having a program with computer executable instructions for performing the method according to the present invention, if the program is loaded on a computer.

The present invention furthermore addresses the above needs in providing a computer system for the case specific information retrieval and for implementing the inventive method according to the present invention.

DETAILED DESCRIPTION OF THE INVENTION

Aspects of a method and a system for case-specific information retrieval are described hereinafter. In the following description, meaning of specific details is given to provide a thorough understanding of embodiments of the invention. One skilled in the relevant art will recognize, however, that the invention can be practiced without one or more of the specific details, or with other methods, modules, entities etc. In other instances, well-known structures, computer related functions or operations are not shown or described in detail, as they will be understood by those skilled in the art.

Figure 1:
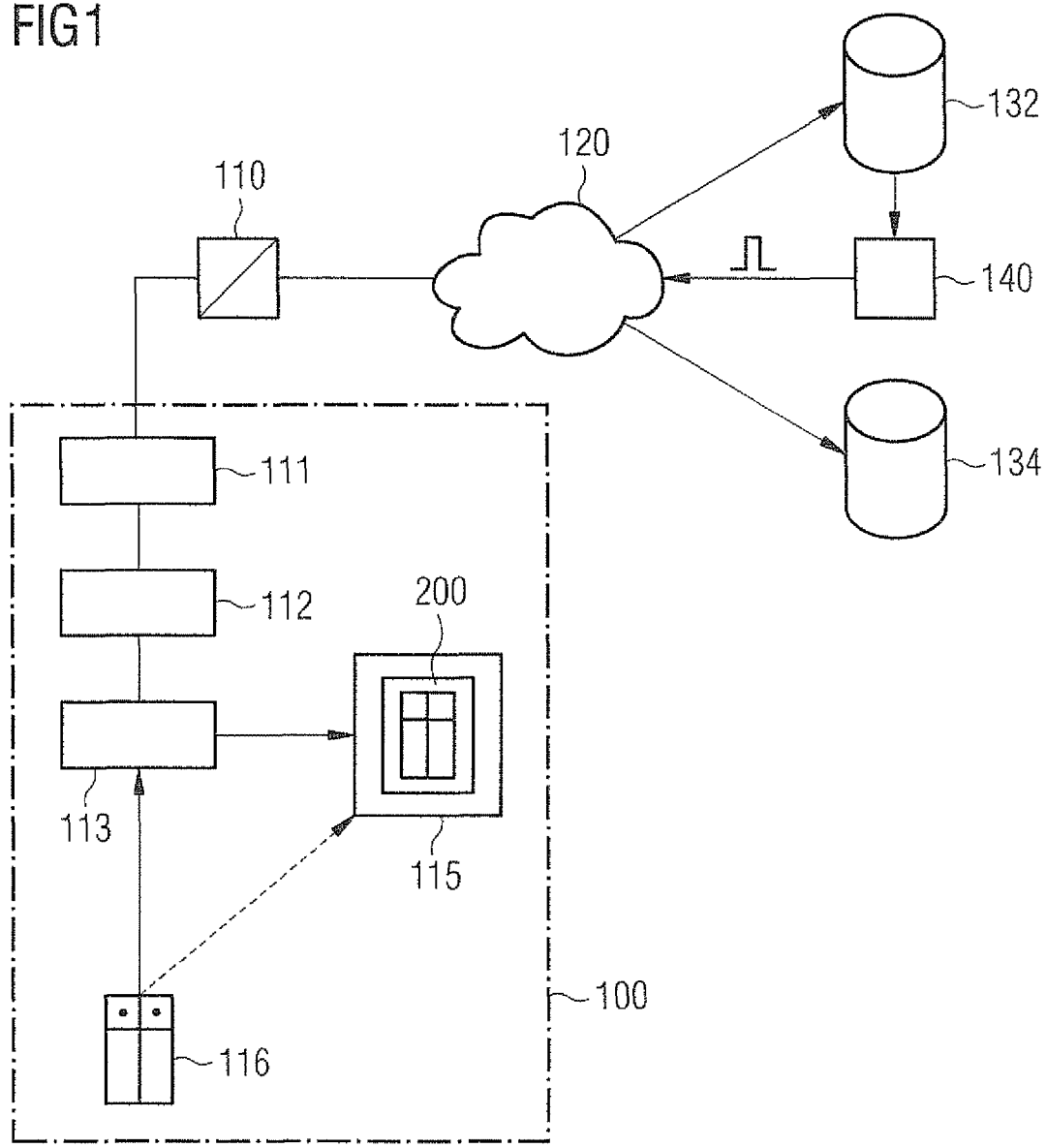
FIG. 1 is a block diagram which illustrates the basic components of a computer system for case specific information retrieval according to one aspect of the present invention.

FIG. 1 shows a schematic block diagram with the basic components of the system for case specific information retrieval according to one aspect of the present invention.

A workstation 100 is connected in a communication network 120 to a rule database 132 and a patient database 134. The workstation 100 comprises a screen 115 and a pointing device in following referred to as a mouse 116. The mouse 116 is operative in controlling via a UI (User Interface) controller 113 a user interface 200 displayed on the screen 115.

At the workstation 100 there are arranged a database accessing module 110 for accessing patient related information stored on a patient database 134 via the communication network 120 and for accessing medical guidelines related information, held in a rules database 132.

For processing the accessed information there is arranged at the workstation 100 a data capturing module 111 in communication with a pattern matcher 112 which in turn communicates with the UI-Controller 113.

The accessed guideline related information and the patient related information are displayed on the inventive graphical user interface 200 in response to control signals from the UI-controller 113 which in turn is controlled by the pattern matcher 112. The pattern matcher 112 matches the guidelines related information and the patient related information captured by the data capturing module 111.

The specific embodiment according to the present invention as shown in FIG. 1 is arranged in a client-sided architecture. However a server-sided arrangement is also in the scope of the present invention.

Furthermore, there is provided a monitoring module 140 for monitoring updates in the rules database 132.

In case an update is detected an update signal is forwarded via the communication network 120 to the workstation 100 in order to inform the data capturing model 111 and/or the database accessing module about the update. Responsive to this updating signal the rules database 132 is being accessed again by the database accessing module 110. Updated data in the rule database 132 is retrieved and captured by the data capturing model 111 and forwarded to the pattern matcher 112 and eventually to the UI controller 113.

In this way the system makes sure that the information displayed on the graphic user interface 200 always reflects the most up-to-date medical knowledge embodied in the medical guideline related information on the rules database 132. The conditions for updating the guidelines database 132, as well as the patient database may be predefined according to a set of patterns. There might be an event-based updating (for example, each time a new data set is being detected) or a time-schedule-based updating (pre-definable time phase for updating).

Processing of the accessed information takes place on the client-side, that is, on the workstation 100. According to another aspect of the present invention processing is executed on the server-side that is to say on a server to which the workstation 100 connects when making a request for accessing the information. This server can be the same as a database server used for running the rules database 132 and the patient database 134. However the server for processing the accessed information may also be arranged separately from the database servers.

Furthermore, it is immaterial for the present invention for the rules database 132 and the patient database 134 to be arranged as two separate databases. The guidelines related information and the patient related information can also be provided as a single "super database" without departing from the scope of the present invention.

The operation and the interrelationships between modules and subsystems as shown in FIG. 1 will now be explained in more detail, at the example of a medical practitioner, referred to as "the user", who wishes to retrieve and to display case specific information with respect to a patient the user is currently examining.

The user, upon providing the proper access authorization, logs onto the workstation 100.

The user then provides a patient ID and/or a patient name suitable for accessing and retrieving patient related information from the patient database 134.

The user also provides information related to current symptoms and current lab data such as a blood sugar level, etc.

The patient related information is essentially an electronic health record (EHR) holding information about the patient's sex, age and previous conditions.

The patient related information, upon accessing the patient database 134 via the database accessing module 110, is captured by the data capturing module 111 as associative array—also known as "hash". The associative array may be nested. An exemplary representation of a nested associative array holding the patient related information is given by the following string:

[sex→'m'; age→'65'; . . . ;

previous_conditions→

[1990→,STROKE'; 1995→'DIABETES M.'; 1997→'ANGINA PECTORIS'];

[current_lab_values→[HAEMO→'123'; . . . ]]

Each key has a value. For example the key "age" has the value '65'. The system interprets the key-value-pair "age/'65'" for example as "the patient being currently 65 years old".

The accessing and capturing of the patient related information according to the present invention is implemented in the PHP scripting language. The PHP language includes a number of database accessing modules suitable for various types of databases. Furthermore, PHP is able to express number of dedicated data structures for example the nested associative array introduced above. Alternative embodiments, however, might also use other mechanisms for accessing databases.

After or simultaneously to the accessing of the patient related data on database 134 the system accesses and retrieves the guidelines related information in the rule database 132, in a similar manner.

The rules represent medical or clinical knowledge as pairs of at least an antecedent and a corresponding consequent. The antecedent represents a specific disease, a group of diseases and/or previous conditions and/or lab values.

The consequents represent medical actions to be taken if the conditions of the antecedent are fulfilled.

The medical actions are for example medications or further diagnostic steps such as a recommendation to acquire further images using a specific modality and configurations thereof are examples of such a consequent.

An exemplary embodiment of the rules comprising pairs of antecedents and consequents are rows in a relational database, each row having various fields.

The fields are Identifications (IDs) for a disease, a code for a corresponding disease or a condition, a code or a number of codes for the corresponding medications to be administered and other fields indicating procedures, diagnostic steps and/or risk factors.

The following provides a schematic representation of such a row from the rule database 132:

| ID | Condition | Medication | Lab Data | Procedures | Diagnosis | Risk Factors |
|---|---|---|---|---|---|---|

The system for case specific retrieval according to the present invention accesses and retrieves all or a predefined number of rows from the rule database 134.

Accessing, retrieving and data capturing of the rows might again be implemented as PHP scripts, using readily available database accessing modules for PHP corresponding to the type of database server on which the databases 132, 134 is running.

For the purposes of controlling and composing the graphic user interface 200 the "Flex Environment" by Adobe® might be used.

The pattern matcher 112 and the UI controller 113 are arranged as modules within the Flex Environment's "Flex builder".

The captured rows from the rule database 132 and the patient database 134 are both passed as associative arrays to the pattern matcher 112. The pattern matcher 112 matches the values corresponding to the keys in the associated array representing the patient related information to the values corresponding to the entries in the fields of the captured row or rows. The pattern matcher 112 matches the values as strings.

Figure 2:
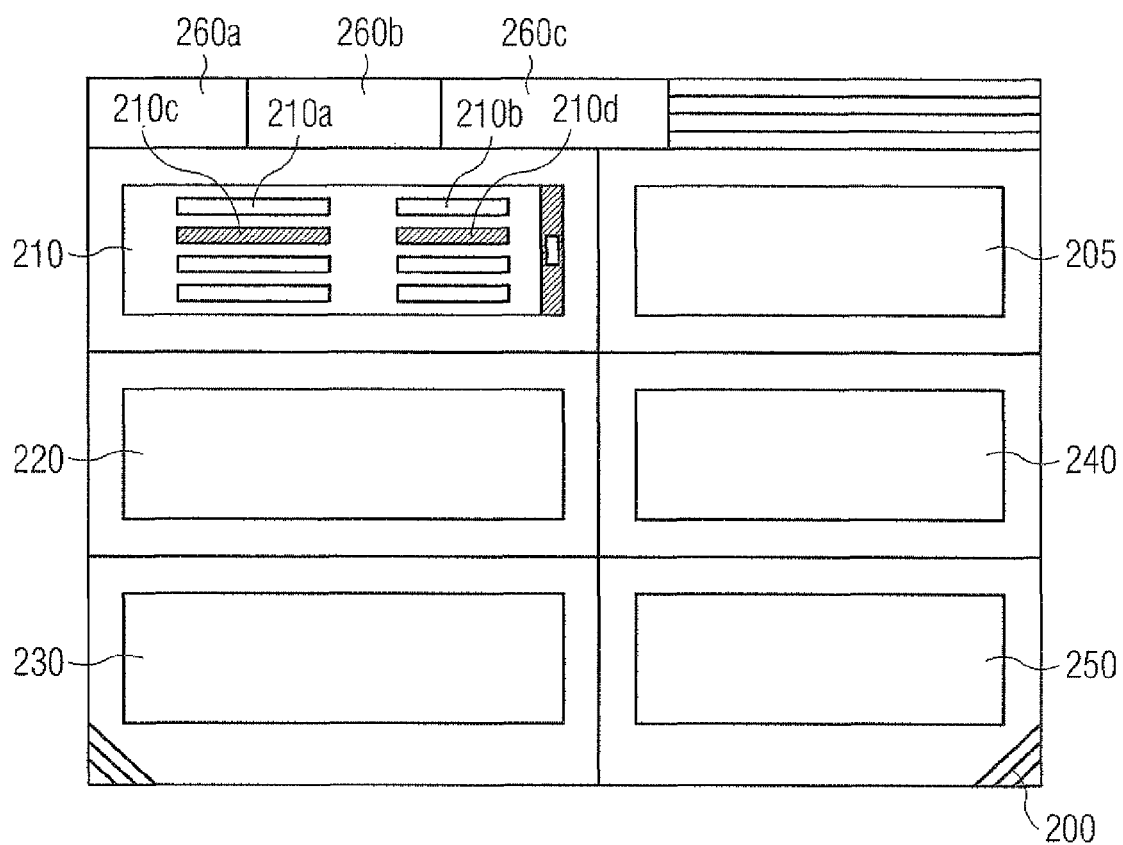
FIG. 2 shows a schematic view of a user interface for the retrieval of case specific information according to one aspect of the present invention.

Once a match has been detected by the pattern matcher 112 a corresponding matching signal is passed to the UI controller 113. The matching signal encodes the row and the fields of that row in which the match occurred. The entries from the row are then rendered by the UI controller 113 as a subpanel 210 of the user interface 200 as shown in FIG. 2. The matching signal effects setting the matching values in bold type as shown in "match" text fields 210c and 120d. Other values from the rows are set in regular type into other text fields in the subpanel 210, for example "non-match" text fields 210a and 210b.

The patient related information itself is set in a separate patient subpanel 205 of the user interface 200. Other disease specific information from other ones of the retrieved rows are set in the "disease specific" subpanels 220, 230, 240 and 250 in a manner similar to the exemplary subpanel 210 explained above.

The "patient" subpanel 210 and the "disease" subpanels 210-250 allow for an integrated view on the medical applicability of the medical knowledge in the "disease" subpanels 210-250 to the patient specific information in the "patient" subpanel 210. The applicability is indicated by the values set in bold type within subpanels 210-250.

By showing the matching values within the subpanels 210-250 in bold type or in any other highlighted manner, it is easier for the user to establish how the medical knowledge relates or applies to the patient related data in the "patient" subpanel 205.

There are further provided control buttons 260a-b for sorting the retrieved guideline related information within the "disease" subpanels 210-250 according to pre-definable criteria or for changing into an expert view for example by rearranging the "disease" subpanels 210-250 and/or the "patient" subpanel 205.

A monitoring module 140 is arranged to detect updates in the rule database 132. The monitoring module interfaces with updating functionalities specific to the rule database 132. Once a new row has been added or information in existing rows has been edited or modified a corresponding updating signal is forwarded to the workstation 100. The monitoring by the monitoring module 140 is either triggered by a time signal or other pre-definable criteria.

The updating signal is intercepted by the database access module 110 and/or the data capturing module 111. In response to the updating signal the rule database 132 is re-accessed and the new row(s) or the edited rows are retrieved from the database 132 and captured by the database accessing module 110 and the data capturing module 111.

The pattern matcher 112 matches the newly added rows or edited rows against the patient related information retrieved earlier and displayed in the "patient" subpanel 205.

If a match is detected the guideline related information displayed on the "disease" subpanels 210-250 is updated. The updating is, for example, done by adding or removing the information and/or by re-setting information in bold type in the "disease" subpanels 210-250 affected by the updated guideline related information.

According to one aspect of the present invention the pattern matcher 112 can be configured to operate in different matching modes. A default mode is a "100% matching mode", in which strings are "hard"-matched on a character-by-character basis. This mode can be used if the strings encoding the entries in the rows and in the patient related information comply with a controlled vocabulary. If no controlled vocabulary is used when populating the rule database 132 or the patient database 134 the pattern match 112 is configurable to implement a "fuzzy" matching mode. According to this mode, wildcards or other matching templates are used to enable fuzzy or partial matching.

According to yet another aspect of the present invention the pattern matcher 112 is configurable by the user to assign weights to matches found in pre-definable ones of the rows. The assigning of weights implements a weighted matching mode which allows the user express preferences in matching guideline-related information against patient related information.

According to another aspect of the present invention there are arranged learning modules in communication with the user interface 200. The learning modules intercept interactions between the user and the user interface 200, based on the user's actions. The learning modules implement suitably configured neural networks or genetic algorithms enabling to learn from a behavior of the user. The behaviour is defined by the user's actions with respect to the user's interface 200. The learning modules change or adapt the guidelines related information in response to the user's configuration of the weights in the weighting matching mode. The learning modules are arranged (not shown) between the workstation 100 and the rule database 132 and effectively provide a feed back loop to the medical knowledge in the rule database 132. In this way the system utilizes personal or clinical medical knowledge of the user to improve the medical knowledge represented in the rule database 132.

According to another aspect of the present invention the system provides a further functionality of risk calculations based on the patient related information in subpanel 205 of the user interface 200.

The user selects one or more of "disease" subpanels 210-250.

Values corresponding to the keys "sex", "age", "lab values" from the associative array and shown in the patient" subpanel 205 are passed to a calculation module (not shown) upon clicking "CALCULATE RISK FACTOR" control button 260*d*. The calculation module compares those values with corresponding values from the selected "disease" subpanels 210-250 and calculates a risk factor. This risk factor is then displayed in a pop-up window, informing the user about a likelihood of the patient having a corresponding condition.

According to another aspect of the present invention current lab values shown on the "patient" subpanel 205 are automatically flagged as abnormal in case non-standard deviations from any one of average values specified in the "disease"

subpanels 210-250 are detected.

The user is provided with information concerning a degree of the deviation by a tool-tip popping up upon having the pointer of the mouse hovering over the flagged values.

Figure 3:
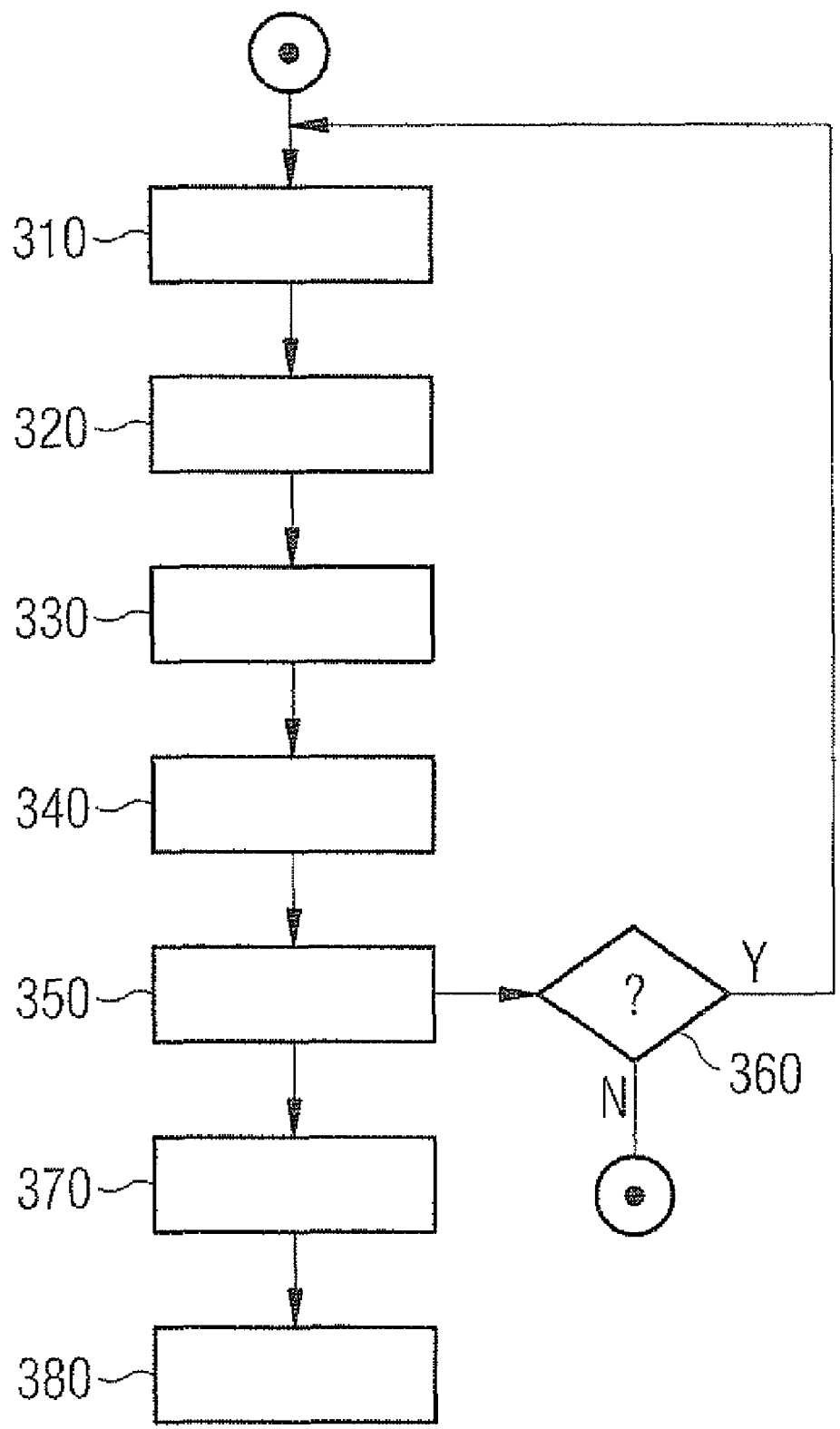
FIG. 3 is a basic flowchart of a method for case specific information retrieval according to one aspect of the present invention.

FIG. 3 shows a schematic flowchart representing the logic flow of the method for retrieving case specific information according to one aspect of the present invention.

In steps 310 and 320 the guidelines related information and the patient related information are accessed and retrieved upon user input at the workstation 100.

In steps 330 the accessed guideline related information is matched against the accessed patient related information. Matched pairs of information items are retrieved in step 340 along with the non-matching information items.

The retrieved information items are displayed in step 350 on the graphic user interface 200 in subpanels 205 to 250. The method according to present invention can be implemented either in a server-sided or a client-sided environment. The steps of matching 330 and the steps retrieving 340 can be interchanged.

In step 360 the rule database 132 is monitored for updates. In case an update is detected updated information items are passed to the workstation 100 in order to correspondingly update the display at step 350, after going through steps 310-340 again. At step 370 the displayed patient related information and the guidelines related information are compared.

In case of deviation the corresponding patient related information items are flagged in step 380.

The above description of illustrated embodiments of the invention is not intended to be exhaustive or to limit the invention to precise forms disclosed. While specific embodiments of, and examples for, the invention are described herein for illustrative purposes various equivalent modifications are possible within the scope of the invention and can be made without a deviating from the spirit and scope of the invention.

The method is described in terms of software modules arranged on suitable computer readable-medium storage devices. Alternatively, it is possible to implement the method according to the invention in hardware or hardware modules. The hardware modules are then adapted to perform the functionality of the steps of the method. Furthermore, it is possible to have a combination of hardware and software modules.

What I claim is:

1. A method for case-specific information retrieval from a medical database system, the information comprising at least two categories, clinical guidelines related information and patient related information, the method comprising:
    (a) accessing a rules database for retrieval of the clinical guidelines related information, wherein the clinical guidelines related information comprises structured rules representing medical or clinical knowledge as antecedent/consequent pairs, wherein the antecedent represents at least one of a disease, a condition, or lab data, and the corresponding consequent represents medical actions are taken when conditions of the antecedent are fulfilled;

(b) accessing a database for retrieval of the patient related information stored as electronic data files;

(c) matching the patient related information for a specific patient and the clinical guidelines related information via a pattern matcher using comparative data operations, wherein the patient related information further includes current patient data comprising symptoms or lab data for the specific patient;

(d) displaying and integrated view comprising a first subpanel showing the accessed clinical guidelines related information, a second subpanel showing the accessed patient related information, and one or more disease subpanels showing disease specific information, wherein matched values are displayed in a highlighted manner in the subpanels to establish how the medical or clinical knowledge applies to the patient related information and other unmatched values remain in regular type; and (e) detecting updates in the rules database and re-accessing the rules database for retrieval of the clinical guidelines related information and repeating the matching step and displaying step to incorporate any updates therein.

2. The method of claim 1, wherein the clinical guidelines related information and patient related information are stored in different segments of the same or in different databases.

3. The method of claim 1, further comprising displaying case specific information specific to a geographical area or nationality for the specific patient and qualifying certain curative actions with respect to geo-specific physiological characteristics of patients from that geographical area.

4. The method of claim 1, wherein detecting updates is triggered by time or by other configurable events.

5. The method of claim 1, wherein the matching comprises either a hard-matched character-by-character mode for use with controlled vocabulary or a fuzzy matching mode for use without controlled vocabulary to allow for wildcards and partial matching.

6. The method of claim 1, further comprising
comparing the accessed clinical guidelines related information and the patient related information with reference values and in case the accessed clinical guidelines related information and the patient related information do not comply with the reference values;
flagging the non-compliant guidelines related information and the patient related information; and
providing a degree of deviation from the reference values.

7. A computer readable medium having computer-executable instructions for performing the method according to claim 1.

8. A computer system for case-specific information retrieval from a medical database system, the information comprising at least two categories, clinical guidelines related information and patient related information, the system comprising:
a rule database storing the clinical guidelines related information on a storage device, wherein the clinical guidelines related information comprises structured rules representing medical or clinical knowledge as antecedent/consequent pairs, wherein the antecedent represents at least one of a disease, a condition, or lab data, and the corresponding consequent represents medical actions are taken when conditions of the antecedent are fulfilled;
a patient database storing the patient related information stored as electronic data files;
a computer workstation having a user interface in communication with the rule database and the patient database, wherein the computer workstation accesses the rule database and the patient database via a database access module and thereafter processes the accessed information via modules comprising:

(a) a data capture module for capturing the accessed clinical guidelines related information and patient related information from the rule database and the patient database;

(b) a pattern matcher for matching the patient related information for a specific patient and the clinical guidelines related information using comparative data operations, wherein the patient related information further includes current patient data comprising symptoms or lab data for the specific patient;

a graphical display in communication with the computer workstation for displaying an integrated view comprising a first subpanel showing the accessed clinical guidelines related information, a second subpanel showing the accessed patient related information, and one or more disease subpanels showing disease specific information, wherein matched values are displayed in a highlighted manner in the subpanels to establish how the medical or clinical knowledge applies to the patient related information and other unmatched values remain in regular type; and a monitoring module in communication with the rules database for monitoring updates to the rules database and sending a data to the computer workstation to re-access the rule database and processes the re-accessed information to incorporate any updates therein.

9. The computer system of claim 8, wherein the monitoring module is triggered by time or by other configurable events.

10. The method of claim 1, further comprising calculating risk factors for selected disease by comparing certain key values from the patient related information to corresponding values from a selected disease subpanel and displaying the risk factor to a user, thereby informing the user about a likelihood of the specific patient having the selected disease.

11. The method of claim 10, wherein the key values from the patient related information comprise one or more of sex, age, and lab values.

12. The computer system of claim 8, further comprising a calculation module for calculating risk factors for a selected disease by comparing certain key values from the patient related information to corresponding values from a selected disease subpanel and displaying the risk factor to a user, thereby informing the user about a likelihood of the specific patient having the selected disease.

13. The computer system of claim 12, wherein the key values from the patient related information comprise one or more of sex, age, and lab values.

* * * * *